United States Patent
Iwasaki et al.

(10) Patent No.: US 8,217,209 B2
(45) Date of Patent: Jul. 10, 2012

(54) PROCESS FOR PRODUCTION OF GAS HYDRATE

(75) Inventors: Toru Iwasaki, Ichihara (JP); Masahiro Takahashi, Ichihara (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 375 days.

(21) Appl. No.: 12/085,377

(22) PCT Filed: Nov. 29, 2006

(86) PCT No.: PCT/JP2006/323845
§ 371 (c)(1),
(2), (4) Date: May 22, 2008

(87) PCT Pub. No.: WO2007/063915
PCT Pub. Date: Jun. 7, 2007

(65) Prior Publication Data
US 2009/0287028 A1 Nov. 19, 2009

(30) Foreign Application Priority Data

Nov. 29, 2005 (JP) ................. 2005-343245

(51) Int. Cl.
C07C 7/20 (2006.01)
C07C 9/00 (2006.01)
(52) U.S. Cl. ........................................ 585/15
(58) Field of Classification Search ............... 585/15
See application file for complete search history.

(56) References Cited

U.S. PATENT DOCUMENTS

| 5,536,893 A | * | 7/1996 | Gudmundsson ............. 585/15 |
| 5,964,093 A | * | 10/1999 | Heinemann et al. ........... 62/45.1 |
| 6,028,234 A | * | 2/2000 | Heinemann et al. ........... 585/15 |
| 6,111,155 A | * | 8/2000 | Williams et al. ............. 585/15 |
| 6,180,843 B1 | * | 1/2001 | Heinemann et al. .......... 585/15 |
| 6,855,852 B1 | * | 2/2005 | Jackson et al. ............... 585/15 |
| 7,371,907 B2 | * | 5/2008 | Lokshin et al. .............. 585/15 |

FOREIGN PATENT DOCUMENTS

| JP | 2000-303083 A | 10/2000 |
| JP | 2001-072615 A | 3/2001 |
| JP | 2001-280592 A | 10/2001 |
| JP | 2003-105362 A | 4/2003 |
| JP | 2005-201286 A | 7/2005 |
| JP | 2005-320454 A | 11/2008 |

* cited by examiner

*Primary Examiner* — Ellen McAvoy
(74) *Attorney, Agent, or Firm* — Kubovcik & Kubovcik

(57) ABSTRACT

Disclosed is a process for production of a gas hydrate, wherein the process comprises a gas hydrate production step, a cooling step, a depressurizing step and a re-cooling step. In the cooling step, the temperature (T) required for the cooling of the gas hydrate is adjusted to a temperature equal to or higher than a cooling limit temperature (t1+t2) (which is a sum of an equilibrium temperature (t1) of the gas hydrate and a temperature for correction (t2)) and equal to or lower than the freezing point (0° C.).

1 Claim, 4 Drawing Sheets

PROCESS FOR PRODUCTION OF GAS HYDRATE

BACKGROUND OF THE INVENTION

1. Field of the Invention

The present invention relates to a process for production of gas hydrate for producing gas hydrate that is a hydration reaction product of raw material gas and water.

2. Description of the Related Art

The gas hydrate is an icy solid crystal consisting of a water molecule and a gas molecule, and a general term for clathrate hydrate in which the gas molecule is present in a steric cage structured by the water molecules. It is said that the gas hydrate can contain natural gas in an amount as large as approximately 165 Nm$^3$ per unit volume of 1 m$^3$. For this reason, research and development for utilizing the gas hydrate as natural gas transport and storage means are intensively performed.

Advantages of the natural gas being hydrated include: (a) enabling storage and transport under a temperature condition easier than a storage and transport temperature (−163° C.) of liquefied natural gas (LNG) under atmospheric pressure, which has been put into practical use; and (b) enabling durability or heat insulating properties of storage and transport equipment to be significantly simplified because the gas hydrate has self-preservation property.

In general, the gas hydrate can be produced on a lower temperature and higher pressure side of a three-phase equilibrium curve of hydrate, water, and gas. When the gas hydrate is produced from water and raw material gas, it is generally produced under a temperature condition equal to or more than 0° C. and a pressure condition higher than an equilibrium condition. On the other hand, from a perspective of emphasizing economic efficiency, pressure upon storage and transport is preferably lower.

A production condition of the gas hydrate typically includes a pressure of 1 to 5 MPa and a temperature of 0 to 10° C. However, If the gas hydrate having been produced under a pressure condition higher than the equilibrium condition is depressurized to a pressure lower than the equilibrium condition, e.g. to atmospheric pressure for storage or transport, the gas hydrate is decomposed in the process of the depressurization, so that there has been proposed a technique in which the gas hydrate is cooled to below freezing point and extracted with being frozen along with adhered water (see, for example, Patent documents 1 and 2).

The extracted hydrate is superior in economic efficiency if it contains a larger amount of gas, so that it is important to reduce an amount of gas discharged as much as possible in the process of the depressurization. Also, if the gas hydrate is cooled to below the freezing point, refrigeration equipment and running cost cause an increase in burden, and therefore we have checked from experiment a most appropriate extent to which the gas hydrate is cooled upon depressurization (pressure release) of the gas hydrate. The experimental results are illustrated in FIGS. 5 and 6.

It turns out from the diagrams that a decomposition amount of gas hydrate varies depending on a type, or concentration of additive gas mixed into methane, or a cooling temperature. For example, if the additive gas is ethane, the gas hydrate is hardly decomposed at the cooling temperature of −5° C. as illustrated in FIG. 5. However, it also turns out that at the cooling temperature of −10° C., the gas hydrate is decomposed at a rate of approximately 5 to 28%, and at −25° C., the gas hydrate is decomposed at a rate of approximately 1 to 43%.

In addition, if the additive gas is propane, it turns out as illustrated in FIG. 6 that at the cooling temperature of −5° C., the gas hydrate is decomposed at a rate of approximately 3 to 35%; at −10° C., at a rate of approximately 9 to 30%; and at −25° C., at a rate of approximately 1 to 35%.

When the gas hydrate is produced with mixed gas (raw material gas) of methane including ethane and propane component, it turns out that the gas hydrate of which structure types I and II coexist is produced, and the structure type II contains mixed gas of methane and propane, or methane and ethane, of which a concentration in the structure is 20 to 30%.

A self preservation principle of gas hydrate is considered as follows:

(a) When the gas hydrate having been produced under high pressure is frozen and depressurized to be brought into a decomposition condition under atmospheric pressure, the decomposition of the gas hydrate is partially started from its surface, and gas molecules forming the gas hydrate are gasified, as well as a water film covers the gas hydrate surface.

(b) When heat is lost due to the decomposition at the gas hydrate surface, the water film on the gas hydrate surface comes to an ice film which covers the gas hydrate surface.

(c) When the ice film grows to a certain thickness or more, heat exchange between the gas hydrate inside the ice film and the outside is blocked, and therefore the inside gas hydrate is stabilized even under the decomposition condition such as atmospheric pressure.

(d) That is, because the ice film has mechanical strength sufficient to resist pressure of the decomposing gas hydrate, the gas hydrate is stabilized, and further decomposition is suppressed.

Note that, preferably, the decomposition at the gas hydrate surface rapidly progresses to form the ice film on the gas hydrate surface. On the other hand, if the decomposition at the gas hydrate surface slowly progresses, the decomposition progresses to the inside before the ice film is formed on the gas hydrate surface, and consequently the decomposition amount upon depressurization is increased Accordingly, by depressurization at a temperature higher than the equilibrium temperature of the gas hydrate by a certain degree or more, stable ice is formed as a film on the gas hydrate surface upon the depressurization. If a shift in temperature is small, the decomposition slowly progresses, so that the ice growing on the gas hydrate surface does not form a film, and therefore the decomposition amount is increased. From the experimental results, it turns out that by setting the shift in temperature to 40 degrees or more from the equilibrium temperature upon the depressurization, the ice film is formed, and therefore the decomposition is suppressed.

Patent document 1: Japanese patent application Kokai publication No. 2001-280592

Patent document 2: Japanese patent application Kokai publication No. 2003-105362

SUMMARY OF THE INVENTION

The present invention is made on the basis of such knowledge, and an object thereof is to provide a process for production of gas hydrate capable of suppressing the decomposition of the gas hydrate as much as possible in the process of depressurizing (pressure releasing) the gas hydrate and extracting it into the atmosphere.

In order to solve such problem, the present invention is configured as follows:

A process for production of gas hydrate according to claim 1 comprises: a gas hydrate production step of reacting raw material gas and water with each other to produce gas hydrate; a cooling step of cooling the gas hydrate produced in the gas hydrate production step; a depressurizing step of depressurizing the gas hydrate cooled in the cooling step to atmospheric pressure; and a recooling step of recooling the gas hydrate depressurized in the depressurizing step into a storage state, and is characterized in that a gas hydrate cooling temperature T in the cooling step is set to a temperature equal to or more than a lower limit cooling temperature $t_1+t_2$ and equal to or less than the freezing point (0° C.), the lower limit cooling temperature $t_1+t_2$ being an equilibrium temperature $t_1$ of the gas hydrate added with a correction temperature $t_2$.

A process for production of gas hydrate according to claim 2 is characterized in that in claim 1, the correction temperature $t_2$ is set to 40 degrees.

A process for production of gas hydrate according to claim 3 is characterized in that in claim 1, the correction temperature $t_2$ is set to 50 degrees.

A process for production of gas hydrate according to claim 4 is characterized in that in claim 1, a recooling temperature upon recooling of the gas hydrate into the storage state is set to −15° C. to −30° C.

That is, the invention according to claim 1 is a process for production of gas hydrate comprising: a gas hydrate production step of reacting raw material gas and water with each other to produce gas hydrate; a cooling step of cooling the gas hydrate produced in the gas hydrate production step; a depressurizing step of depressurizing the gas hydrate cooled in the cooling step to atmospheric pressure; and a recooling step of recooling the gas hydrate depressurized in the depressurizing step into a storage state, wherein a gas hydrate cooling temperature T in the cooling step is set to a temperature equal to or more than a lower limit cooling temperature $t_1+t_2$ and equal to or less than the freezing point (0° C.), the lower limit cooling temperature $t_1+t_2$ being an equilibrium temperature $t_1$ of the gas hydrate added with a correction temperature $t_2$, so that upon depressurization of the gas hydrate, i.e. upon depressurization from a high-pressure gas hydrate production area to a low-pressure (atmospheric-pressure) gas hydrate storage area, ice film is rapidly formed on a surface of the gas hydrate, and therefore a decomposition amount of the gas hydrate can be significantly suppressed.

Accordingly, loss of contained gas is extremely small upon the depressurization, so that a larger amount of gas can be transported and stored, and therefore economical transport and storage of the gas hydrate becomes possible. Also, according to the invention as defined in claim 1, because the decomposition amount of the gas hydrate is small as described above, a recovery apparatus for recovering the decomposed gas can be miniaturized.

The invention according to claim 2 is adapted such that in claim 1, the correction temperature $t_2$ is set to 40 degrees, so that upon depressurization of the gas hydrate, the ice film is stably formed on the surface of the gas hydrate, and therefore the decomposition amount of the gas hydrate upon the depressurization can be significantly suppressed.

The invention according to claim 3 is adapted such that in claim 1, the correction temperature $t_2$ is set to 50 degrees, so that upon depressurization of the gas hydrate, the ice film is stably formed on the surface of the gas hydrate, and therefore the decomposition amount of the gas hydrate upon the depressurization can be significantly suppressed.

The invention according to claim 4 is adapted such that the recooling temperature upon recooling of the gas hydrate into the storage state is set to −15° C. to −30° C., so that a self preservation effect of the gas hydrate can be utilized to the maximum extent during transport and storage of the gas hydrate to suppress the decomposition of the gas hydrate as much as possible.

Accordingly, the gas hydrate can be transported and stored for a long term without being forcedly cooled during its transport and storage.

DETAILED DESCRIPTION OF THE INVENTION

An embodiment of the present invention will hereinafter be described with the use of the drawings.

Figure 1:
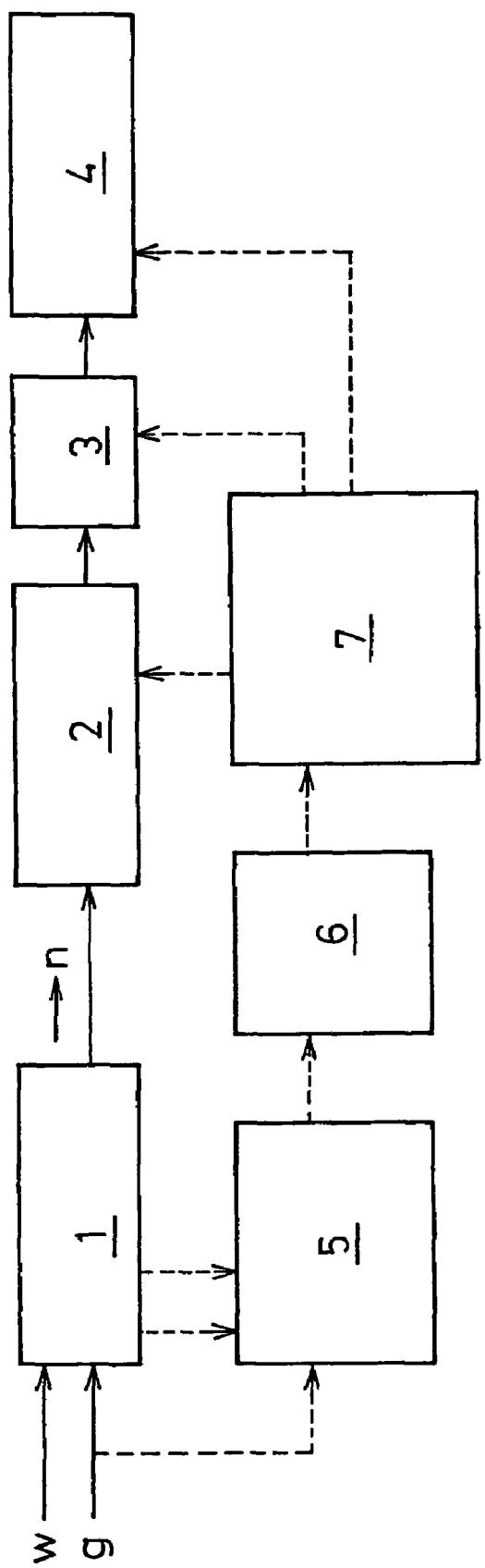
FIG. 1 is a block diagram illustrating a process based on a process for production of gas hydrate according to the present invention.

In FIG. 1, Reference numeral 1 represents a hydrate producing reactor, 2 first cooler, 3 depressurizing device, 4 second cooler, 5 hydrate composition calculator or hydrate analyzer, 6 equilibrium temperature computing device, and 7 cooling/depressurizing/storage temperature setter.

The hydrate composition calculator can include, for example, one calculating a gas hydrate composition from a composition of raw material gas, the other one calculating a gas composition of gas hydrate from a gas composition in a gas phase in the hydrate producing reactor on the basis of an equilibrium calculation program (e.g. CSMHYD), or the like. For information on the equilibrium calculation program (e.g. CSMHYD), see "Clathrate Hydrates of Natural Gases (E. D. Sloan, Jr., Marcel Dekker, Inc., New York, 1998)".

The hydrate composition analyzer can include an analyzer that decomposes gas hydrate sampled from the hydrate producing reactor or an unshown storage tank and analyzes a gas composition by gas chromatography, or the like.

On the other hand, the cooling/depressurizing/storage temperature setter 7 is adapted to set a lower limit cooling temperature $t_1+t_2$ (° C.), which is an equilibrium temperature $t_1$ (° C.) added with a correction temperature $t_2$ (degrees) (e.g. 40 degrees, preferably 50 degrees), as a cooling temperature T(° C.) of the first hydrate cooler 2 and hydrate depressurizing device 3.

The cooling/depressurizing/storage temperature setter 7 also has functions of, if the cooling temperature T (° C.) exceeds the freezing point (0° C.), setting a temperature equal to or less than the freezing point (0° C.) (e.g. −10 to 0° C.) as the cooling temperature of the first hydrate cooler 2 and hydrate depressurizing device 3, and setting a cooling temperature of the second hydrate cooler 4 and storage tank to a predetermined temperature (e.g. −15 to −30° C.).

Specifically, the depressurizing temperature is set depending on a component of the raw material gas as follows: For example, in the case of methane, because the equilibrium temperature is −80° C., a stable extracting temperature preferably has the shift in temperature of 40 degrees from the equilibrium temperature upon extraction. More preferably, it has the shift in temperature of 50 degrees.

In the case of mixed gas, and if the equilibrium temperature is higher than −40° C., the shift in temperature of 40 degrees results in the depressurizing temperature equal to or more than 0° C. If it exceeds 0° C., the surface ice is not formed, so that in such a case, the depressurization should be performed at a highest possible temperature equal to or less than 0° C.

Regarding the equilibrium temperature of mixed gas, because ethane and propane are concentrated to approximately 30% in the case of a gas composition of the structure type II gas hydrate, equilibrium calculation is performed for the case where the gas composition of the gas hydrate reaches this concentration. The equilibrium calculation was applied with the CSMHYD program.

Figure 2:
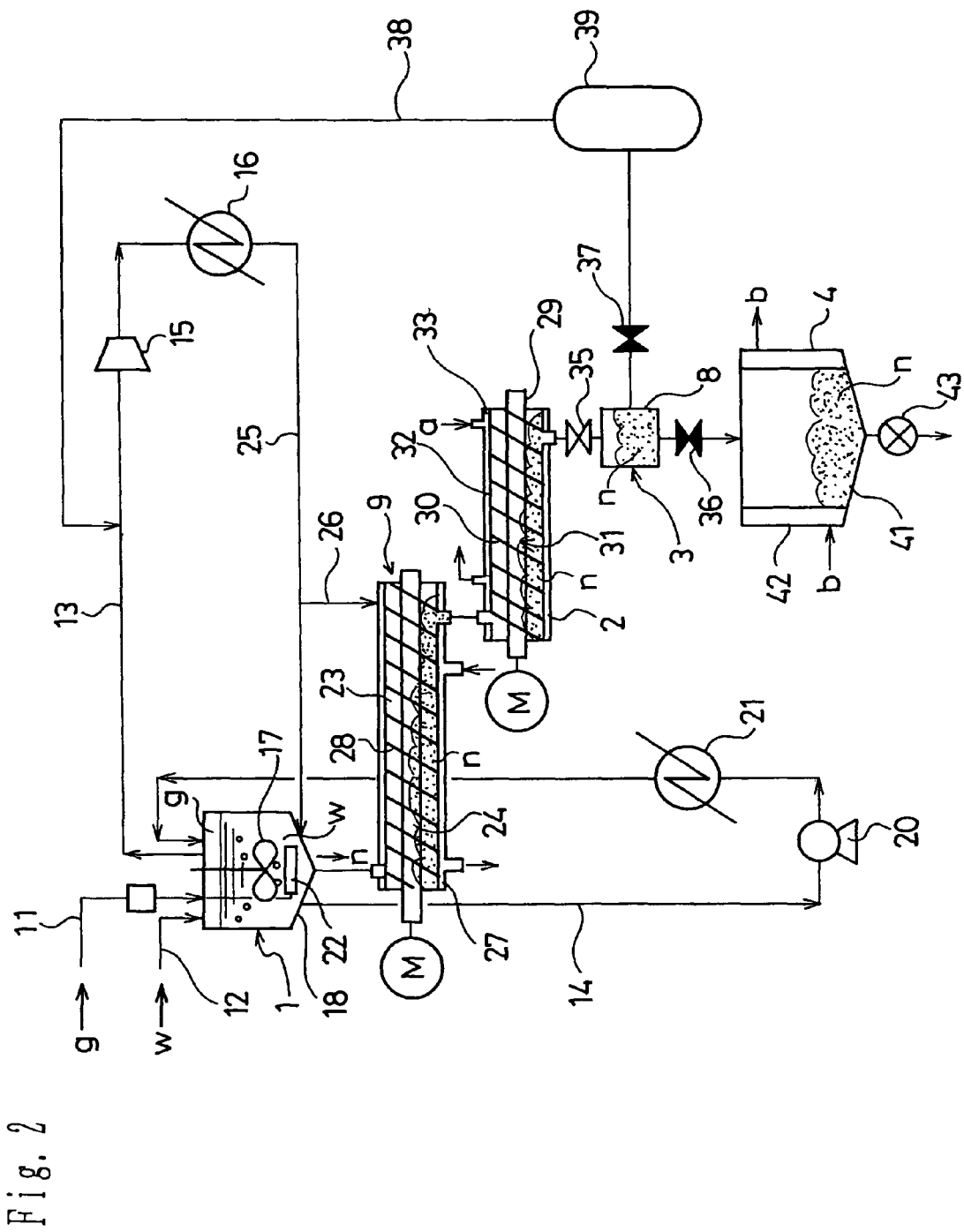
FIG. 2 is a schematic configuration diagram of apparatus applied to perform the process for production of gas hydrate according to the present invention.

In FIG. 2, Reference numeral 1 represents a hydrate producing reactor of a stirring and bubbling type, 2 first cooler of a screw conveyer type, 3 depressurizing device of a lock hopper type, 4 second cooler of a cooling jacket type, and 9 a dehydrator of a hydration type.

The above hydrate producing reactor 1 comprises a raw material gas supply pipe 11, raw material water supply pipe 12, gas circulation path 13, and water circulation path 14. The gas circulation path 13 has a compressor 15 and heat exchanger 16, and is adapted to boost unreacted raw material gas g in the hydrate producing reactor 1 to a predetermined pressure (e.g. 4 to 6 MPa) with the use of the compressor 15, and then cool it to a predetermined temperature (e.g. 0 to 10° C.) with the use of the heat exchanger 16 to give it back into the hydrate producing reactor 1. The hydrate producing reactor 1 is adapted to stir in a reactor 18 with a stirrer 17 as well as removing reaction heat with an unshown cooling jacket.

On the other hand, the water circulation path 14 has a pump 20 and heat exchanger 21, and circulates unreacted water w in the hydrate producing reactor 1 with the use of the pump 20. It is also adapted, upon the circulation, to cool the circulation water to a predetermined temperature (e.g. 0 to 7° C.) with the use of the heat exchanger 21.

The above dehydrator of a hydration type 9 has a shaft 24 having a large number of stirring blades 28 in a barrel 23, as well as allowing the barrel 23 to connect to a branch pipe 26 branched from a pipeline 25 of the gas circulation path 13. The raw material gas g supplied into the barrel 23 via the branch pipe 26 reacts with water attached to gas hydrate n to newly produce gas hydrate, i.e. the gas hydrate is dehydrated. In addition, reaction heat is adapted to be removed with a cooling jacket 27 provided outside the barrel 23.

The above first cooler 2 is provided in a barrel 32 with a shaft 31 having a screw blade 30 along a rotary shaft 29, as well as having a cooling jacket 33 outside the barrel 32. It is also adapted to supply refrigerant a to the cooling jacket 33 to cool the dehydrated gas hydrate to a predetermined cooling temperature T° C. If the cooling temperature T° C. exceeds the freezing point (0° C.), the first cooler 2 is adapted to cool the dehydrated gas hydrate to a temperature equal to or less than the freezing point (0° C.). In addition, temperature control of the first cooler 2 is performed by, for example, adjusting a supply amount of the refrigerant a.

The above depressurizing device 3 has a first valve 35 on an upstream side of a pressure resistant container 8, and a second valve 36 on a downstream side thereof. In addition, it is provided with a pressure reducing valve 37 and accumulator 39 in a path 38 making a communicative connection between the pressure resistant container 8 and the gas circulation path 13, and adapted to depressurize the atmosphere of the gas hydrate n supplied to the pressure resistant container 8 from a gas hydrate production pressure to atmospheric pressure.

The above second cooler 4 has a cooling jacket 42 on a side surface of a tank 41, and is adapted to cool the gas hydrate n in the tank 41 to a predetermined temperature (e.g. −15 to −30° C.) with the refrigerant b supplied to the cooling jacket 42. The gas hydrate n cooled by the second hydrate cooler 4 is drawn out to an unshown storage tank with a rotary valve 43. The storage tank does not require cooling means in general, but may comprise forced cooling means as desired.

Next, operations of the above gas hydrate production apparatus are described.

As illustrated in FIG. 2, when the raw material gas (natural gas) g having the predetermined pressure (e.g. 4 to 6 MPa) is supplied from the gas supply pipe 11 while the water w (raw material water) (e.g. water temperature of 0 to 10° C.) in the hydrate producing reactor 1 is stirred with the use of the stirrer 17, the finely bubbled natural gas g discharged from a gas ejector 22 and the water w react with each other to produce natural gas hydrate (hereinafter referred to as "gas hydrate") n.

The gas hydrate n produced in the hydrate producing reactor 1 is subjected to first dehydration with, for example, a gravity dehydrator (not shown). The gas hydrate n subjected to the first dehydration is then subjected to second dehydration with the dehydrator of a hydration type 9. That is, the water w attached to the gas hydrate subjected to the first dehydration is dehydrated because it is reacted with the natural gas g supplied from the gas circulation path 13 when passing through the dehydrator of a hydration type 9, to form the gas hydrate.

The gas hydrate n subjected to the second dehydration with the dehydrator of a hydration type 9 is supplied to the first cooler 2. Then, it is cooled to the predetermined cooling temperature T° C. (e.g. the equilibrium temperature upon the depressurization $t_1$ ° C.+40 degrees, preferably the equilibrium temperature upon the depressurization $t_1$ ° C.+50 degrees) when passing through the first cooler 2. Note that, if the above cooling temperature T° C. exceeds the freezing point (0° C.), the gas hydrate n is cooled to a temperature equal to or less than the freezing point (0° C.) (e.g. −10 to 0° C.).

The gas hydrate n cooled to the predetermined temperature with the first cooler 2 is still exposed to the pressure upon production of the gas hydrate (e.g. 4 to 6 MPa), so that it is depressurized to atmospheric pressure with the depressurizing device of a lock hopper type 3, and then supplied to the second cooler of a cooling jacket type 4.

That is, when the first valve 35 located on the upstream side of the depressurizing device 3 is opened, the gas hydrate n cooled to the predetermined temperature T° C. with the first cooler 2 is supplied to the pressure resistant container 8 of the depressurizing device 3 along with the unreacted natural gas g having the pressure upon production of the gas hydrate (e.g. 4 to 6 MPa).

When the above first valve 35 is closed, and then the pressure reducing valve 37 is opened, the natural gas g accompanying the gas hydrate n is discharged from the pressure reducing valve 37, and pressure in the pressure resistant container 8 is reduced to the atmospheric pressure (0.1 MPa). The natural gas g discharged from the pressure reducing valve 37 is once accumulated in the accumulator 39, and then given back to the gas circulation path 13 via the path 38.

When the above pressure reducing valve 37 is closed, and then the second valve 36 is opened, the gas hydrate n in the pressure resistant container 8 is supplied into the second cooler 4. The gas hydrate n supplied into the second cooler 4 is cooled to a temperature (e.g. −15 to −30° C.) at which the decomposition is most difficult. The gas hydrate n cooled to the predetermined temperature with the second cooler 4 is supplied to an unshown storage tank by the rotary feeder 43.

The gas hydrate supplied to the storage tank has been cooled to the predetermined temperature (e.g. −15 to −30° C.) as described above, so that the self preservation effect is produced to suppress rapid decomposition. Note that an inside of the above storage tank may be forcedly cooled as desired.

EXAMPLES

Example 1

Methane hydrate was produced with the use of 100% methane as the raw material gas. Production and storage conditions are as follows:

| (1) Gas hydrate producing reactor | |
|---|---|
| (a) Production pressure: | 5.4 MPa |
| (b) Production temperature: | 2° C. |

| (2) First cooler | |
|---|---|
| (a) Pressure: | 5.4 MPa |
| (b) Temperature: | −30° C. |

| (3) Depressurizing device | |
|---|---|
| (a) Pressure: | 5.4 MPa → 0.1 MPa |
| (b) Temperature: | −30° C. |

| (4) Storage tank | |
|---|---|
| (a) Pressure: | 0.1 MPa |
| (b) Temperature: | −15 to −30° C. |

In the case of methane, the equilibrium temperature $t_1$ is −80° C., so that if the correction temperature $t_2$ is set to 50 degrees, the temperature of the first cooler T becomes:

$$T = t_1 + t_2 = -80(°C.) + 50 \text{ (degrees)} = -30(°C.).$$

Figure 3:
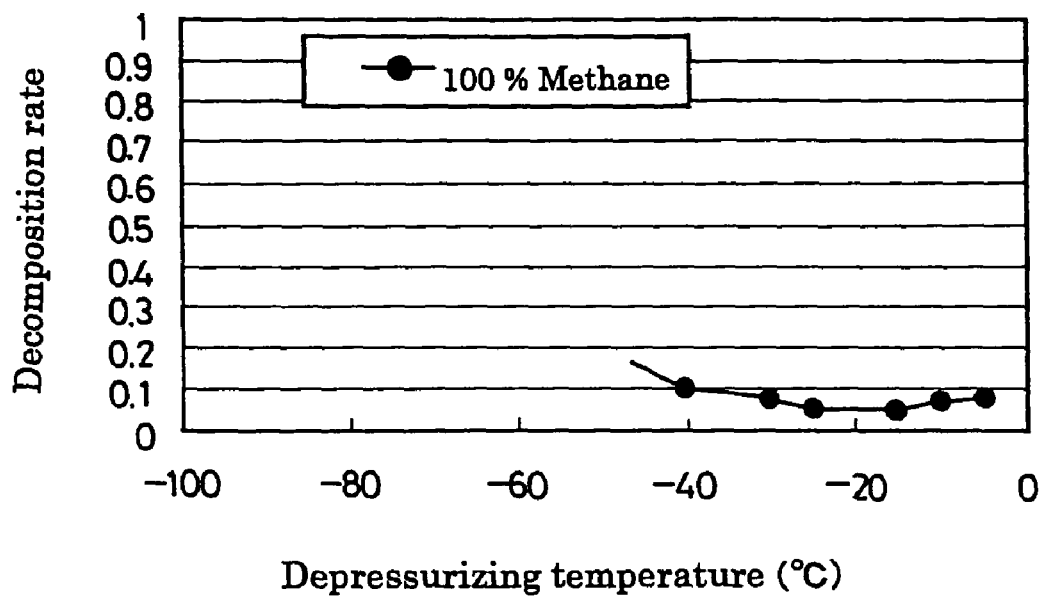
FIG. 3 is a diagram illustrating a relationship between a depressurizing temperature and decomposition rate of methane hydrate.

FIG. 3 illustrates a decomposition rate of the methane hydrate for the case where the temperature of the first cooler T was set to −30° C. It turns out from FIG. 3 that the decomposition rate of the methane hydrate can be suppressed at a rate of 10 to 5%.

Example 2

Methane propane hydrate was produced with the use of mixed gas of 97% methane and 3% propane as the raw material gas. Production and storage conditions are as follows:

| (1) Gas hydrate producing reactor | |
|---|---|
| (a) Production pressure: | 5.4 MPa |
| (b) Production temperature: | 2° C. |

| (2) First cooler | |
|---|---|
| (a) Pressure: | 5.4 MPa |
| (b) Temperature: | −15° C. |

| (3) Depressurizing device | |
|---|---|
| (a) Pressure: | 5.4 MPa → 0.1 MPa |
| (b) Temperature: | −15° C. |

| (4) Storage tank | |
|---|---|
| (a) Pressure: | 0.1 MPa |
| (b) Temperature: | −15 to −30° C. |

In this case, the equilibrium temperature $t_1$ is −65° C., so that if the correction temperature $t_2$ is set to 50 degrees, the temperature of the first cooler T becomes:

$$T = t_1 + t_2 = -65(°C.) + 50 \text{ (degrees)} = -15(°C.).$$

Figure 4:
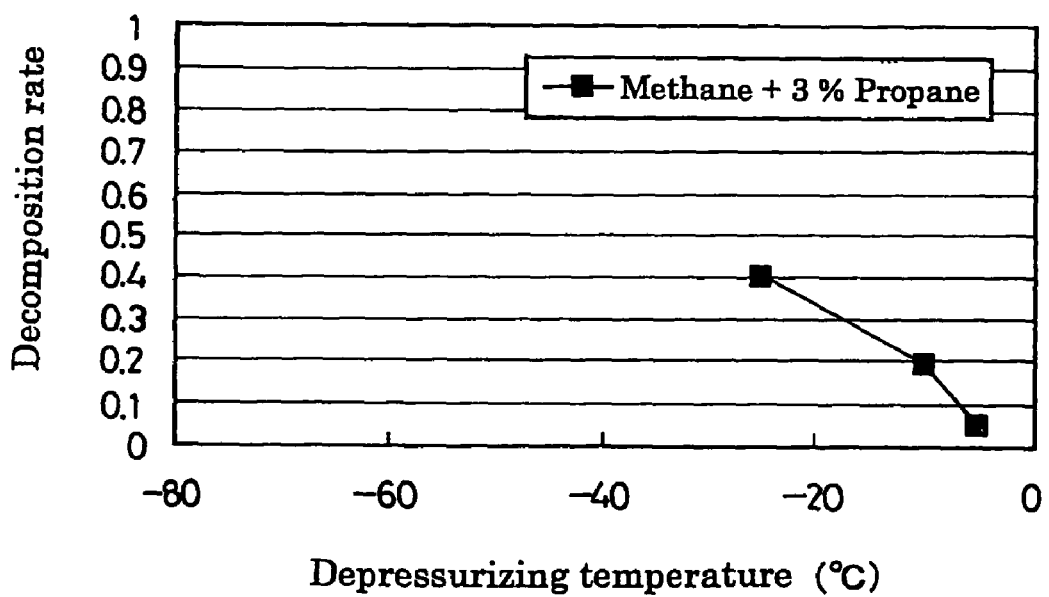
FIG. 4 is a diagram illustrating a relationship between a depressurizing temperature and decomposition rate of mixed gas hydrate in which methane and propane are mixed.
Figure 5:
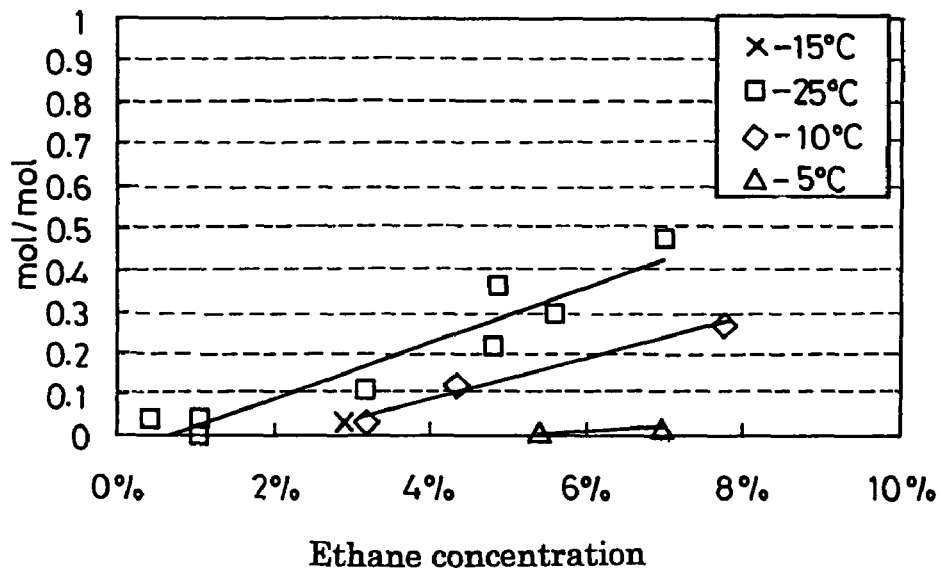
FIG. 5 is a diagram illustrating a decomposition characteristic of mixed gas hydrate in which methane and ethane are mixed.
Figure 6:
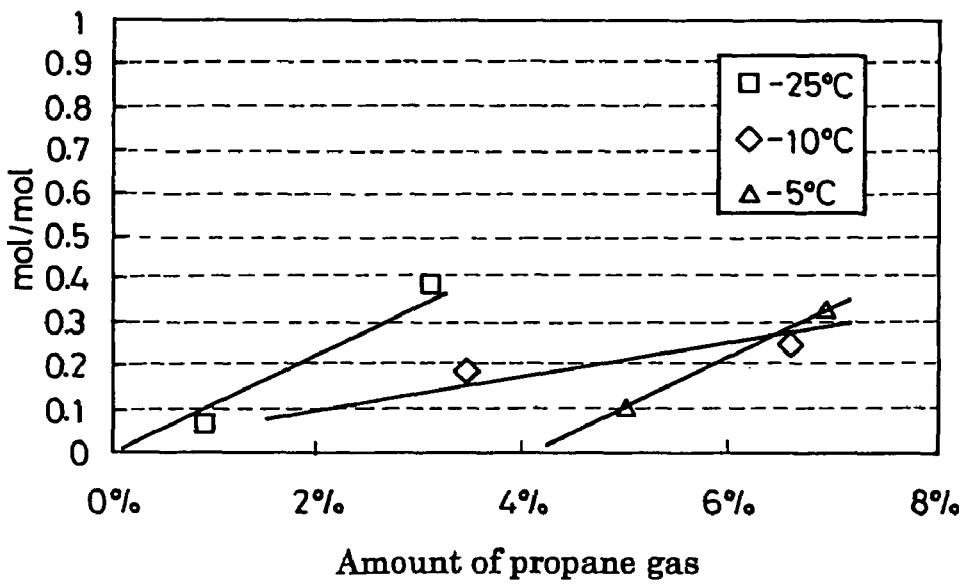
FIG. 6 is a diagram illustrating a decomposition characteristic of the mixed gas hydrate in which methane and propane are mixed.

FIG. 4 illustrates a decomposition rate of the methane propane hydrate for the case where the temperature of the first cooler T was set to −15° C. It turns out from FIG. 4 that the decomposition rate of the methane propane hydrate can be suppressed at a rate of 20 to 5%.

Industrial Applicability

The present invention can be appropriately used for production of gas hydrate that is a hydration reaction product of raw material gas and water.

What is claimed is:

1. A process for production of gas hydrate comprising:
a gas hydrate production step of reacting raw material gas and water with each other to produce gas hydrate;
a first cooling step of cooling the gas hydrate produced in the gas hydrate production step;
a depressurizing step of depressurizing the gas hydrate cooled in the first cooling step to atmospheric pressure; and
a second cooling step of recooling the gas hydrate depressurized in the depressurizing step into a storage state, wherein
a gas hydrate cooling temperature T (° C.) in the first cooling step is set to a temperature equal to a lower limit cooling temperature t1 (° C.)+t2 (° C.), the lower limit cooling temperature t1 (° C.)+t2 (° C.) being a methane equilibrium temperature t1 (° C.) or an equilibrium temperature t1 (° C.) of a gas mixture consisting of methane and propane, forming the gas hydrate, added with a correction temperature t2 (° C.) depending on a component of the gas hydrate, the correction temperature t2 being set to 40° C. or 50° C., and when the gas hydrate cooling temperature T (° C.) in the first cooling step is more than the freezing point (0° C.), the gas hydrate cooling temperature T (° C.) is set to a temperature range of −10° C. to 0° C.

* * * * *